US012700337B1

(12) United States Patent
Persinger et al.

(10) Patent No.: US 12,700,337 B1
(45) Date of Patent: *Aug. 4, 2026

(54) APPARATUS AND METHOD FOR REDUCING PHOTOPHOBIA IN ELECTRONIC SCREENS

(71) Applicant: Enhanced Vision Systems, Inc., Clearwater, FL (US)

(72) Inventors: Joel Persinger, Wesley Chapel, FL (US); Robert Steinberger, Palm Harbor, FL (US); Joseph Kenyon, Gainesville, FL (US)

(73) Assignee: Enhanced Vision Systems, Inc., Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/819,285

(22) Filed: Aug. 29, 2024

Related U.S. Application Data

(63) Continuation of application No. 17/964,954, filed on Oct. 13, 2022, now Pat. No. 12,080,213.

(60) Provisional application No. 63/255,274, filed on Oct. 13, 2021.

(51) Int. Cl.
| | |
|---|---|
| *G09G 3/20* | (2006.01) |
| *A61N 5/06* | (2006.01) |
| *G09G 5/36* | (2006.01) |

(52) U.S. Cl.
CPC ............. *G09G 3/2003* (2013.01); *A61N 5/06* (2013.01); *G09G 5/363* (2013.01); *A61N*

*2005/0663* (2013.01); *G09G 2340/06* (2013.01); *G09G 2380/08* (2013.01)

(58) Field of Classification Search
CPC ............. A61N 5/06; A61N 2005/0663; G09G 3/2003; G09G 5/363; G09G 2340/06; G09G 2380/08
See application file for complete search history.

(56) References Cited

U.S. PATENT DOCUMENTS

| | | | | |
|---|---|---|---|---|
| 10,140,952 | B1 * | 11/2018 | Letourneur | .............. G09G 5/10 |
| 12,080,213 | B2 * | 9/2024 | Persinger | ................. G02B 5/22 |
| 2015/0324981 | A1 * | 11/2015 | Kim | ...................... G06T 7/0014 |
| | | | | 345/619 |
| 2015/0348468 | A1 * | 12/2015 | Chen | .................... G09G 3/3413 |
| | | | | 345/207 |
| 2017/0336545 | A1 * | 11/2017 | Blair | ..................... A61M 21/00 |

* cited by examiner

*Primary Examiner* — Mihir K Rayan
(74) *Attorney, Agent, or Firm* — Dennemeyer & Associates LLC

(57) ABSTRACT

Disclosed is an apparatus and method for combating light sensitivity, or photophobia, for people with low vision. Both the apparatus and method filter particular wavelengths of light associated with photophobia. This filtering is achieved while maintaining a luminance that is acceptable to the user and that maintains contrast. The apparatus of the disclosure is a mechanical filter that can be applied over an electronic screen. The method utilizes software and a filtering module associated with either the CPU or GPU of a computer. The filtering module processes a video signal by eliminating certain targeted wavelengths of light.

11 Claims, 4 Drawing Sheets

APPARATUS AND METHOD FOR REDUCING PHOTOPHOBIA IN ELECTRONIC SCREENS

CROSS REFERENCE TO RELATED APPLICATIONS

This is a continuation application that claims priority to U.S. patent application Ser. No. 17/964,954, titled, "Apparatus and Method for Reducing Photophobia in Electronic Screens" filed Oct. 13, 2022; and to U.S. Provisional Patent Application No. 63/255,274 filed Oct. 13, 2021, entitled "Apparatus and Method for Reducing Photophobia in Electronic Screens" by the same inventors.

TECHNICAL FIELD

This disclosure relates to an apparatus and method for photophobic filtering. More particularly, the present disclosure relates to photophobic filtering for electronic screens.

BACKGROUND OF THE INVENTION

Photophobia is a medical symptom that is marked by an abnormal intolerance to light. Individuals suffering from photophobia experience eye pain or discomfort when exposed to bright lights. Photophobia can be caused by a variety of medical conditions, including conditions with a person's nervous system or eyes. Individuals suffering from low vision can also suffer from photophobia. For such individuals, photophobia can be especially debilitating and may result in the inability to complete routine daily tasks.

Various efforts have been made over the years to combat photophobia. For instance, U.S. Pat. No. 10,499,805 to Wilkins discloses a visual stress assessment device. The device includes a plurality of colored light sources and a white light source. A chamber is provided with an interior viewable region that allows the user to observe the emitted lights. The chamber is designed to induce visual stress in the user. Appropriate tinted lenses can be selected based upon specific responses provided by the user.

Reduced luminance, to some extent, assists in reducing eye pain. However, reducing luminance also reduces contrast, which in turn, makes it more difficult to view finer details. Accordingly, solutions for combating photophobia that are based upon reduced luminance alone are not ideal. It has been demonstrated that photophobia correlates to particular wavelengths of light entering the eye. These particular wavelengths can be targeted to combat photophobia. The present disclosure relates to targeting these wavelengths in electronic screens. Various hardware and software solutions are disclosed.

SUMMARY OF THE INVENTION

This disclosure relates an apparatus and method for combating photophobia in electronic screens.

An advantage of the present disclosure involves utilizing a physical filter that is placed over an electronic screen with the filter targeting particular wavelengths associated with photophobia.

Another advantage is realized by reducing or eliminating the wavelengths associated with photophobia prior to the images being presented upon a screen.

In one embodiment, the disclosure achieves this by reducing or eliminating selected wavelengths of light via the graphics processing unit (GPU) or the central processing unit (CPU) of a computer.

One advantage is realized by providing a software implementation that systematically filters out the wavelengths of light associated with photophobia; in one possible embodiment, this entails filtering (via software) 100% of wavelengths that are less than 400 nm and 71% of wavelengths between 400-500 nm.

A further advantage is attained by filtering select wavelengths of light while at the same time maintaining a high total luminance.

The disclosed method also benefits from converting from the RGB to the HSL color space prior to making any luminance adjustments.

Still yet other advantages are presented by allowing the user to wear glasses that incorporate physical filters for removing the wavelengths most commonly associated with photophobia.

Finally, an advantage of the present disclosure is realized by incorporating photophobic filters into contact lenses, whereby the degree of filtering can be varied across the surface of the lens to thereby vary the degree of exposure by retinal location. This is advantageous as it allows the amount of exposure to be controlled within a specific retinal location.

Various embodiments of the disclosure may have none, some, or all of these advantages. Other technical advantages of the present disclosure will be readily apparent to one skilled in the art.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

PARTS LIST

20 Portable Electronic Device
22 Filter for Magnifier Device
24 Glasses
26 Filter for Glasses
28 Filtered Contact Lens
32 CPU
34 GPU
36 Screen
38 Filtering Module

DETAILED DESCRIPTION OF THE DRAWINGS

The present disclosure relates to an apparatus and method for combating light sensitivity, or photophobia, in electronic screens. The system and method can be employed by anyone suffering from photophobia, but is ideally used by individuals with low vision. Both the apparatus and method filter particular wavelengths of light associated with photophobia. This filtering is achieved while maintaining a luminance and contrast that is acceptable to the user. To achieve this, adjustments to total luminance can also be made. The apparatus of the disclosure is a mechanical filter that can be applied over an electronic screen. This filter can likewise be applied to glasses or contact lenses. The method utilizes software and a filtering module associated with either the CPU or GPU of a computer. The filtering module processes a video or image signal by eliminating certain targeted wavelengths of light.

Some prior approaches to combating photophobia have relied upon reducing luminance transmittance in an effort to reduce a user's light sensitivity. The problem with this approach is that any reduction in luminance yields a corresponding reduction in contrast. This lack of contrast, in turn, presents other problems for low vision users. The present disclosure overcomes this by maintaining high luminance levels while targeting the specific wavelengths of light known to be associated with photophobia.

Specifically, it has been found that for wavelengths below 460 nanometers ("nm") photophobia increases as the wavelength decreases. This relationship is known from published studies such as Stringham et. al. 2003. More specific relationships between wavelength and photophobia have also been discovered; for example, it has been demonstrated that the effects of photophobia can be ameliorated by filtering 100% of wavelengths below 400 nm and 71% of the wavelengths between 400-500 nm. It has been found that with such targeted filtering photophobia can be reduced by as much as 95% while at the same time maintaining a total luminance that is above 74.5%. As explained below, adjustments to total luminance can be made as needed to faithfully reproduce images or video.

Figure 1:
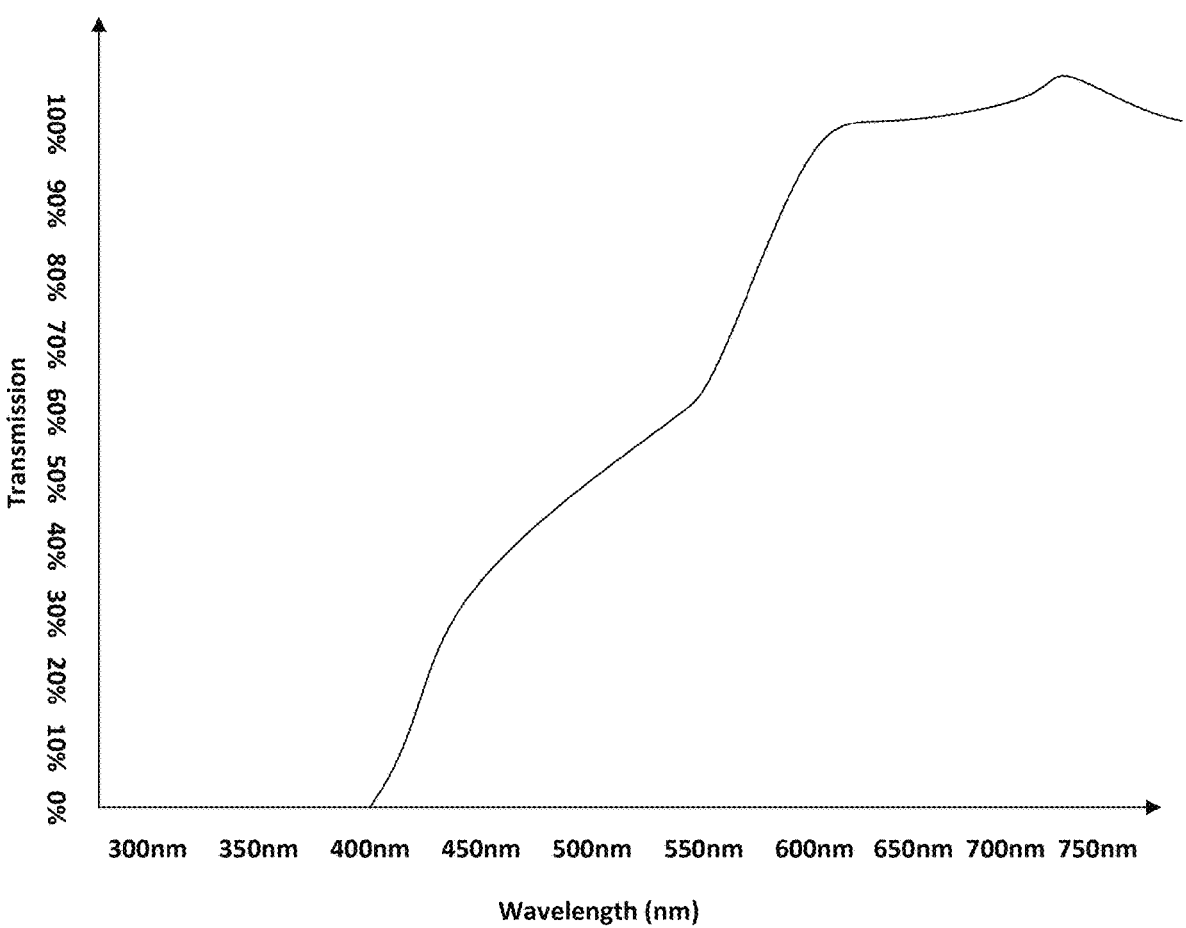
FIG. 1 is wavelength curve that plots the wavelength of light (x-axis) against the transmission or luminance of light (y-axis).

This relationship between luminance (or transmission) and wavelength is demonstrated in FIG. 1. It should be noted that FIG. 1 is just but one of a variety of different wavelength curves that can be employed to combat photophobia. The particular wavelength curve employed may depend upon, for example, the screen resolution, the images/video being displayed, and a user's unique light sensitivity. This disclosure is not intended to be limited to any specific wavelength cure.

Figure 2:
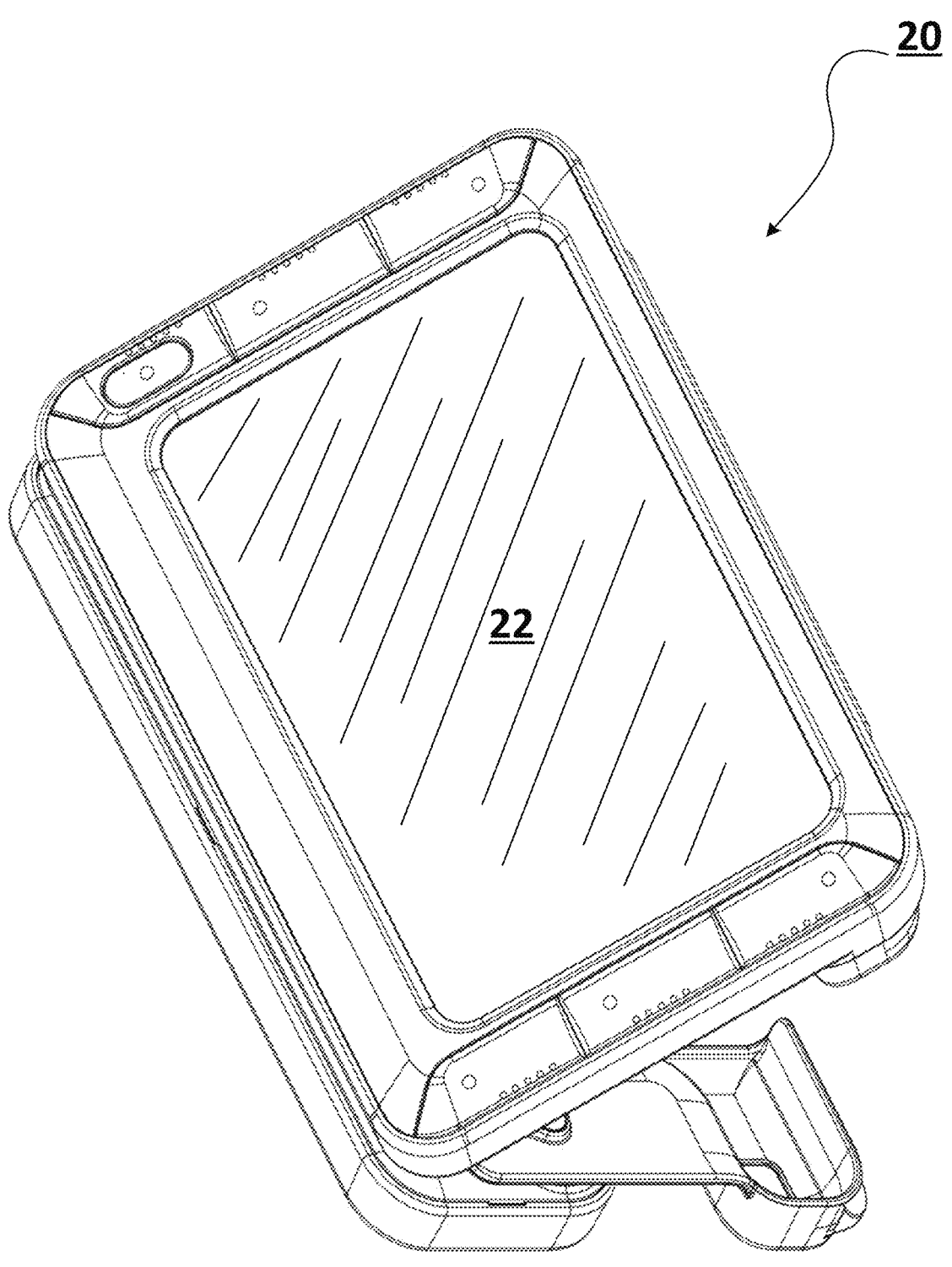
FIG. 2 is a perspective view of a portable electronic device with a physical filter placed over the screen.

The apparatus of the present disclosure is illustrated in connection with FIG. 2. This figure illustrates a portable electronic device 20 with a screen. More specifically, FIG. 2 illustrates a portable electronic magnifier that would typically be employed by a low vision user. However, any of a wide variety of electronic devices and users would benefit from the teachings of this disclosure and the present disclosure is in no way limited to devices for low vision users. As illustrated, a physical filter 22 is applied over top of the electronic screen. Filter 22 is designed to optically filter out wavelengths in the 400-500 nm range, and more specifically to filter the wavelengths to match the curve of FIG. 1. Those of ordinary skill in the art will appreciate the characteristics of a filter needed for such filtration. Filter 22 could either be applied to device 20 during the manufacturing process or it could be applied by the user as an add-on accessory. The benefit of this latter approach would be to allow the filter to be removed as needed and to allow different filters to be employed to suit the particular needs of the user.

Figure 3:
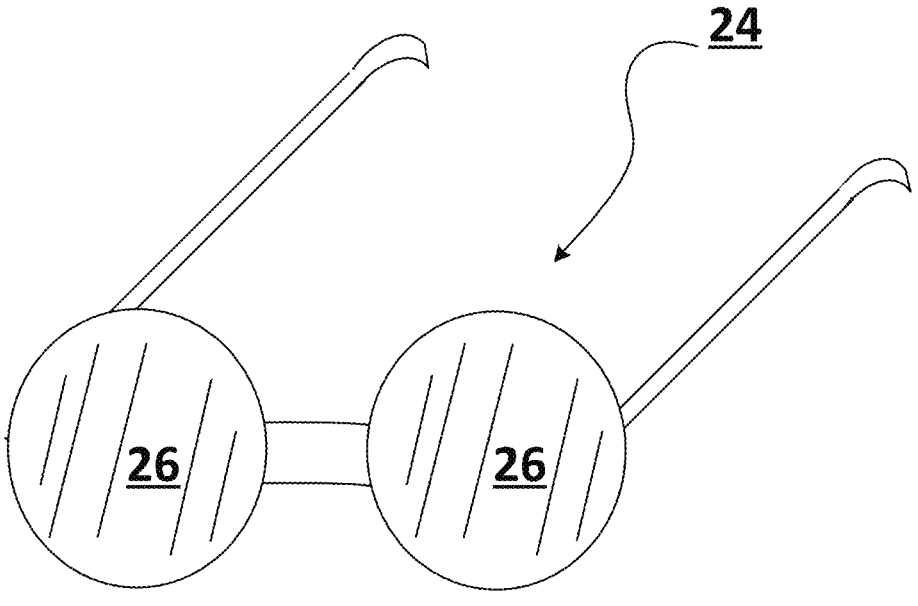
FIG. 3 is a perspective view of glasses employing a physical photophobia filter.
Figure 4:
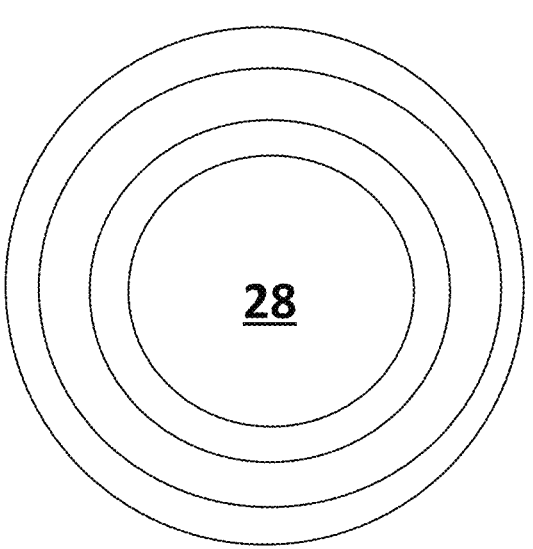
FIG. 4 is a perspective view of a contact lens employing a photophobia filter with varying degrees of filtration across the surface of the lens.

As noted in FIG. 3, it is also within the scope of the present disclosure to apply filters 26 to glasses 24 that are worn by the user. Filters 26 could be applied as a film over the existing lenses. Alternatively, the lenses could be crafted to incorporate the desired filtering. In still yet another embodiment, and as depicted in FIG. 4, photophobic filters can be incorporated into contact lenses 28. Contact lens 28 could incorporate a filter that varies across the lens surface. The would provide the advantage of changing the degree of filtration for different locations over the user's retina. This is important given the known relationship between photophobic symptoms and retinal eccentricity.

Figure 5:
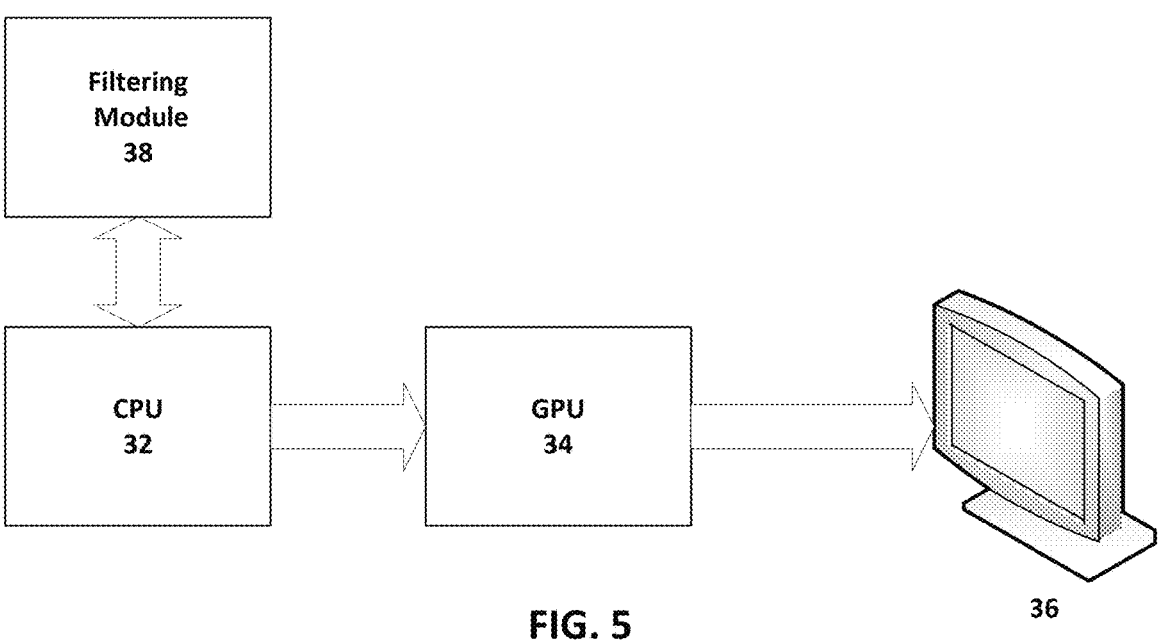
FIG. 5 is a diagram of a filtering module operating in conjunction with a central processing unit (CPU).
Figure 6:
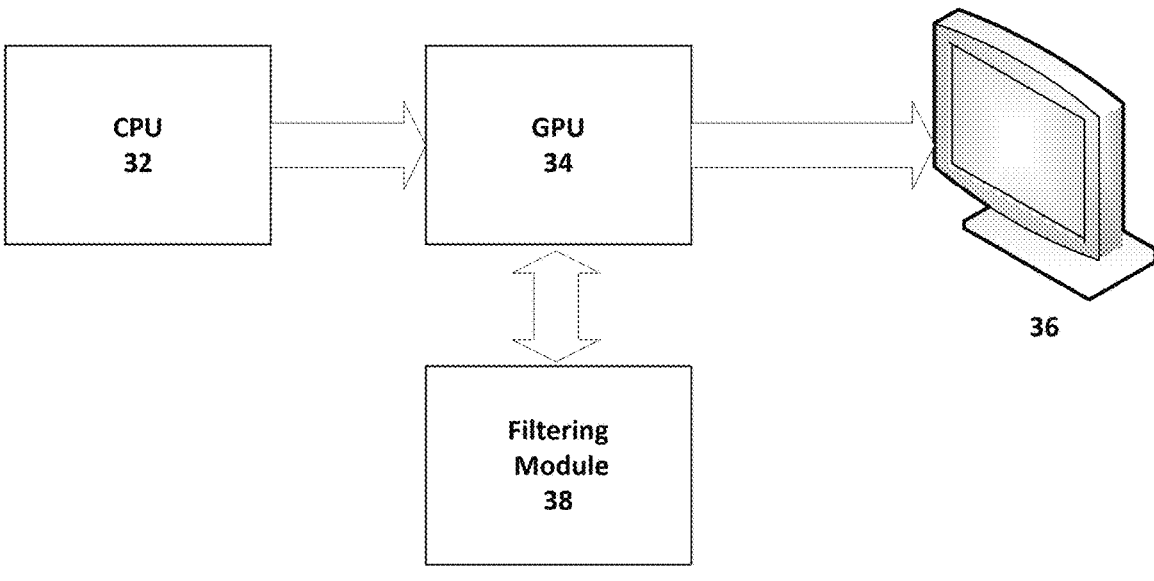
FIG. 6 is a diagram of a filtering module operating in conjunction with a graphics processing unit (GPU).

FIGS. 5 and 6 illustrate two potential software implementations of the present disclosure. These figures broadly disclose how a video or image signal is processed by a Central Processing Unit (CPU 32) and a Graphics Processing Unit (GPU 34) prior to being displayed on a screen 36. Screen 36 can be any of a variety of screens, such as a computer monitor, television screen, or a kiosk terminal. In each case, the video or image signal applied to the screen would be intercepted and processed via a filtering module 38. By way of the processing module 38, any light within the targeted frequencies would be eliminated. In particular, module 38 employs a polynomial expression that matches the graph of FIG. 1. This could be achieved by clamping the targeted wavelengths to a set limit. Alternatively, the individual frequencies (and the red, green, and blue constituent parts) can be targeted in accordance with the desired wavelength curve. Either way, a targeted filtration of the colors associated with photophobia is ensured.

It may also be necessary to adjust the total luminance levels following the frequency filtering noted above. The goal of these luminance adjustments would be to retain the video/image fidelity and to keep the overall luminance sufficiently high. To achieve this, processing module 38 employs software to first convert colors in the RGB (red, green, blue) color model to the HSL (Hue Saturation Lightness) color model. This conversion allows the lightness or luminance of the signal to be scaled without adversely affecting any color characteristics. Namely, lowering lightness of a color in the RGB color model involves lowering all the color channels, which would adversely impact the resulting colors. This can be avoided by first converting the RGB color model to the HSL color model. The HSL color space allows for the direct scaling of only the luminance of a particular color. This color space conversion, and the luminance scaling, can occur before or after the frequency filtering.

Processing module 38 can be associated with either the CPU 32 (note FIG. 5) or the GPU 34 (note FIG. 6) of a computer. It is also within the scope of the present disclosure to undertake such processing at a lower level, such as in the FPGA or microprocessor. In either event, processing module 38 would apply the particular algorithm to make the necessary wavelength adjustments in real time and before passing the video or image signal to the screen 36 to be viewed by the user. The targeted wavelengths would not be displayed by screen 36. This approach has the advantage of not requiring any mechanical screens. As an additional benefit, the particular wavelength curve employed could be selected altered by the user via an appropriate system setting.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A system for displaying an image configured to reduce instances of photophobia in users who are viewing the image, the image having a contrast and colors, the system comprising:

an electronic screen configured to display the image having contrast and colors;

a filtering unit;

a processing unit configured to execute software programs that process video signals by:

generating a video signal;

converting the video signal from an RGB color model to an HSL color model;

passing the video signal to the filtering unit;

filtering the video signal within the filtering unit to remove any video signals having a wavelength of between approximately 400 nm to 500 nm after converting the video signal from RGB color model to an HSL color model; and displaying the image upon the electronic screen using the filtered video signal, whereby the removal of wavelengths between approximately 400 nm to 500 nm reduces instances of photophobia.

2. The system of claim 1 where the software programs further process the video signal by increasing a luminance of the video signal following the conversion to the HSL color model.

3. The system of claim 1 where the processing unit is a central processing unit ("CPU").

4. The system of claim 1 where the processing unit is a Graphics Processing Unit ("GPU").

5. The system of claim 1 where the software programs further process the video signal by increasing a luminance of the video signal following the conversion to the HSL color model.

6. The system of claim 1 where the processing unit is a central processing unit ("CPU").

7. The system of claim 1 where the processing unit is a Graphics Processing Unit ("GPU").

8. A system for displaying an image configured to reduce instances of photophobia in users who are viewing the image, the image having a contrast and colors, the system comprising:

an electronic screen configured to display the image having contrast and colors;

a filtering unit;

a processing unit configured to execute software programs that process video signals by:

generating a video signal;

converting the video signal from an RGB color model to an HSL color model;

passing the video signal to the filtering unit;

filtering the video signal within the filtering unit to remove targeted wavelengths of light, the targeted wavelengths being determined by a polynomial expression, wherein the polynomial expression removes all wavelengths below 400 nm and 71% of wavelengths between 400 nm to 500 nm; and displaying the image upon the electronic screen using the filtered video signal, whereby the removal of targeted wavelengths reduces instances of photophobia.

9. The system of claim 8 where the polynomial expression removes wavelengths in the range of 400 nm to 500 nm.

10. A system for displaying an image while reducing instances of photophobia in users viewing the image, the system comprising:

an electronic screen configured to display the image having contrast and colors;

a filtering unit;

a processing unit configured to execute software programs that process video signals by:

generating a video signal;

passing the video signal to the filtering unit;

filtering the video signal within the filtering unit to remove any video signals having a wavelength of between approximately 400 nm to 500 nm;

converting the video signal from an RGB color model to an HSL color model after performing the step of filtering the video signal;

displaying the image on the electronic screen using the filtered video signal, whereby the removal of wavelengths between approximately 400 nm to 500 nm reduces instances of photophobia.

11. A system for displaying an image while reducing instances of photophobia in users viewing the image, the system comprising:

an electronic screen configured to display the image having contrast and colors;

a filtering unit;

a processing unit configured to execute software programs that process video signals by:

generating an RGB video signal;

passing the RGB video signal to the filtering unit;

converting the RGB video signal to an HSL video signal within the filtering unit, the conversion allowing the luminance of the HSL video signal to be decreased or increased without changing the colors of the image;

filtering the HSL video signal to remove any HSL video signals having a wavelength below approximately 500 nm;

increasing the total luminance of the filtered HSL video signal;

displaying the image upon the electronic screen using the filtered HSL video signal with increased luminance, whereby the removal of wavelengths below approximately 500 nm reduces instances of photophobia while increasing the luminance maintains the image contrast.

* * * * *